United States Patent [19]

DeNiro et al.

[11] Patent Number: 4,585,416

[45] Date of Patent: Apr. 29, 1986

[54] DEVICE FOR CLEANING TEETH AND MASSAGING GUMS

[76] Inventors: Richard G. DeNiro, 1118 E. Adams, Orange, Calif. 92667; Thomas M. Raines, 1727 Willowwood, Apt. C, Anaheim, Calif. 92806; Donald B. Raines, 737 Tennyson Ave., Placentia, Calif. 92670; Joseph B. Raines, 16651 Huggins Ave., Yorba Linda, Calif. 92686

[21] Appl. No.: 602,137

[22] Filed: Apr. 19, 1984

[51] Int. Cl.⁴ .............................................. A61C 5/00
[52] U.S. Cl. ................................. 433/140; 128/62 A
[58] Field of Search ....................... 433/215, 140, 216; 128/67, 62 A; 15/167 R

[56] References Cited

U.S. PATENT DOCUMENTS

| | | | |
|---|---|---|---|
| 1,691,785 | 11/1928 | Remensnyder | 128/62 A |
| 2,172,998 | 9/1939 | Grout | 433/140 |
| 2,284,200 | 5/1942 | Gruss | 128/62 A |
| 3,043,295 | 6/1962 | Ward | 128/62 A |
| 3,853,412 | 12/1974 | Griffin | 128/62 A |
| 3,874,084 | 4/1975 | Cole | 128/62 A |

FOREIGN PATENT DOCUMENTS 7810061  4/1979  Netherlands ..................... 128/62 A

*Primary Examiner*—John J. Wilson
*Attorney, Agent, or Firm*—Knobbe, Martens, Olson & Bear

[57] ABSTRACT

A device is disclosed for simultaneously cleaning teeth, cheeks, lips and the tongue and massaging gums. The device is placed between the teeth and operates in response to chewing action. It can optionally be used with a dentifrice.

16 Claims, 23 Drawing Figures

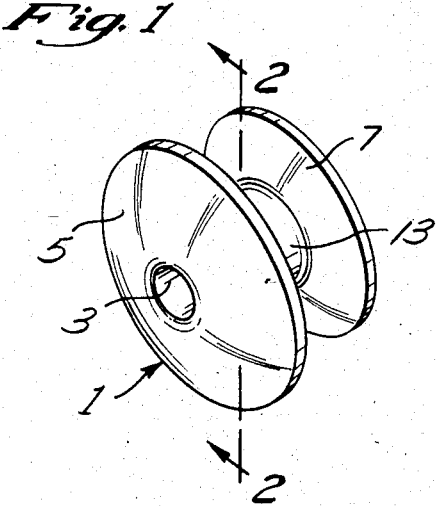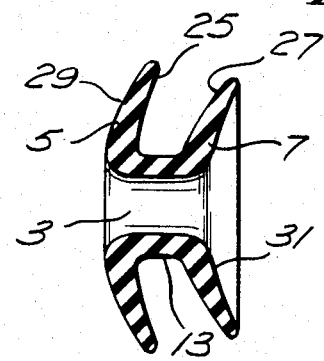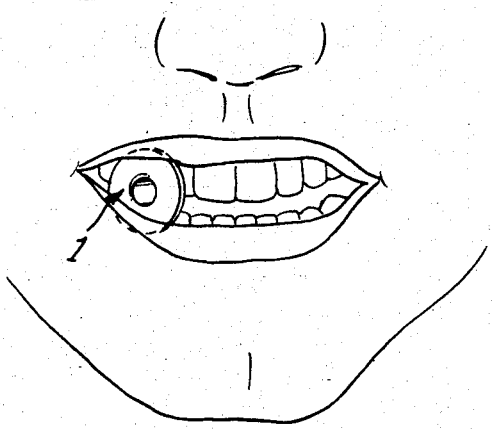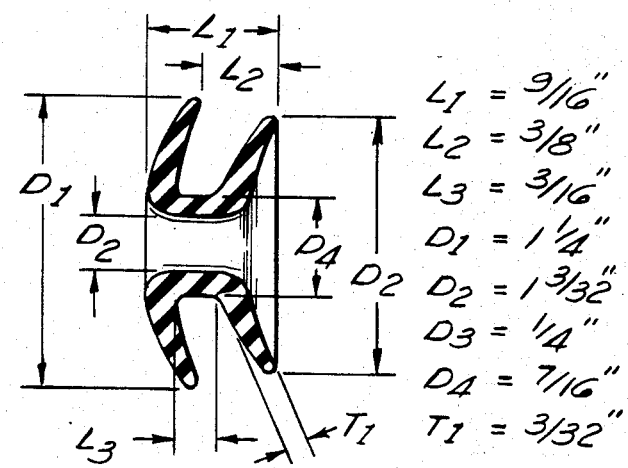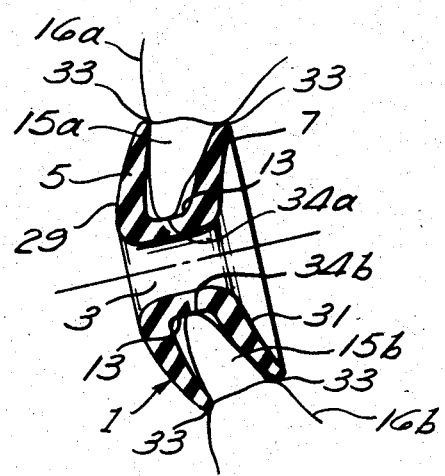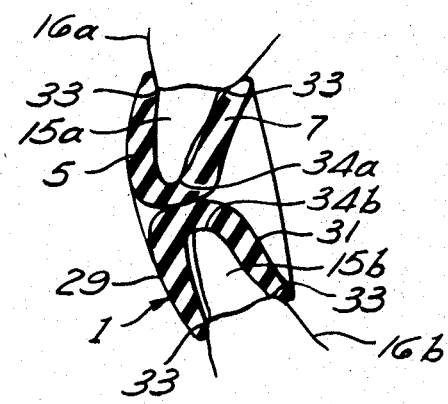

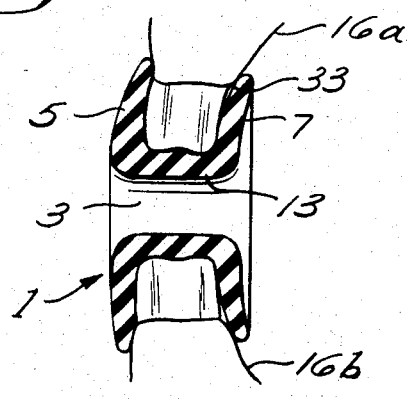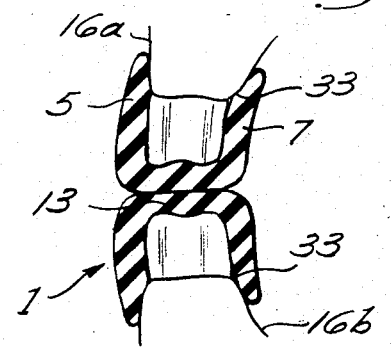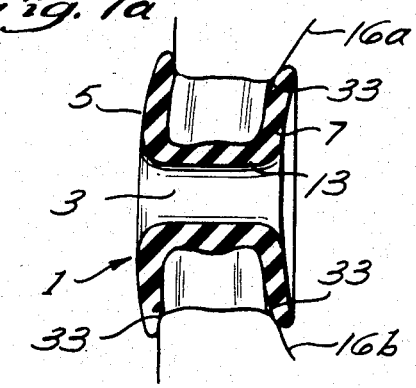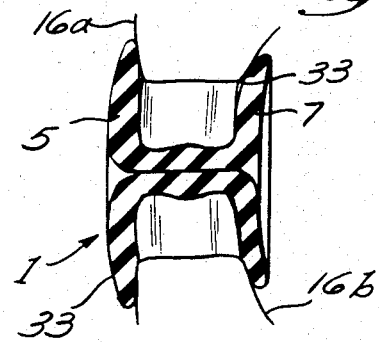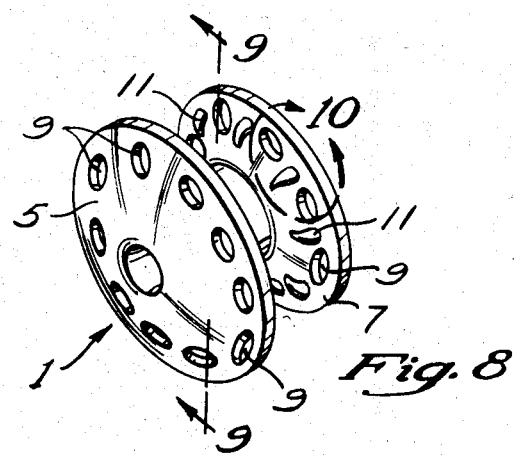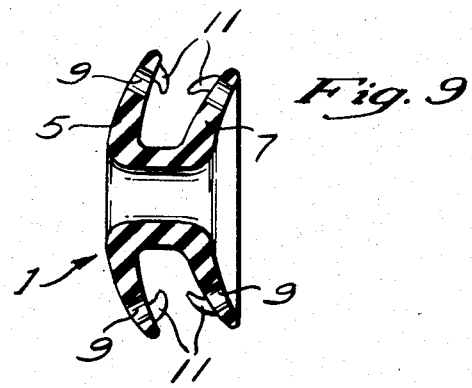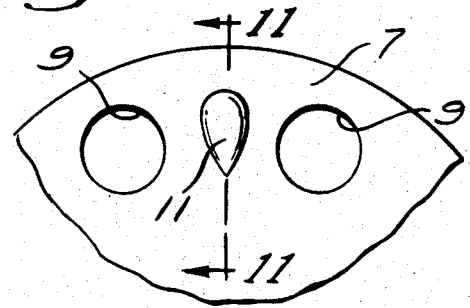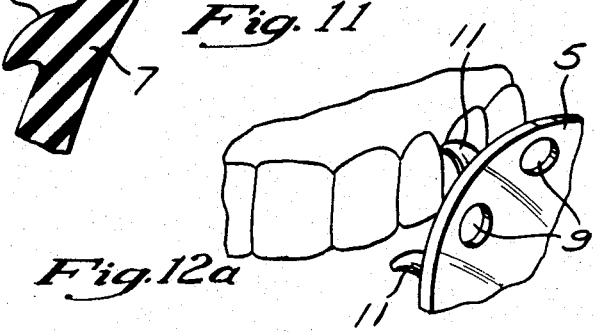

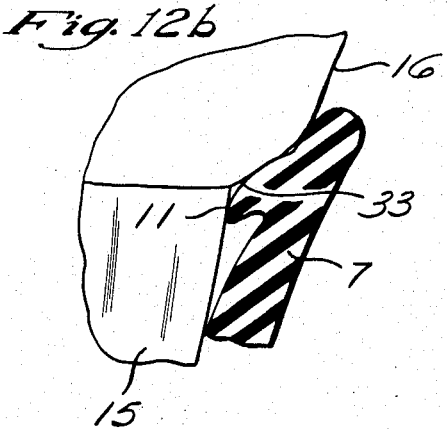
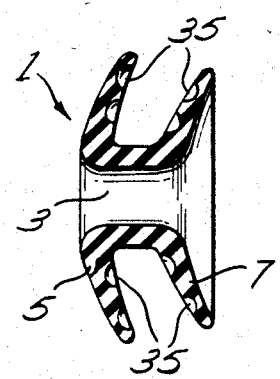
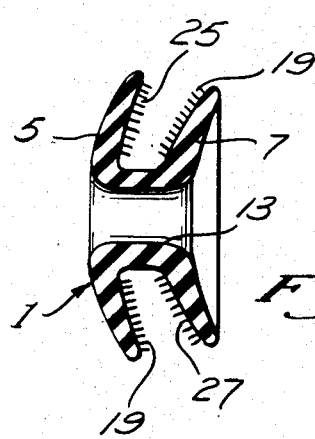
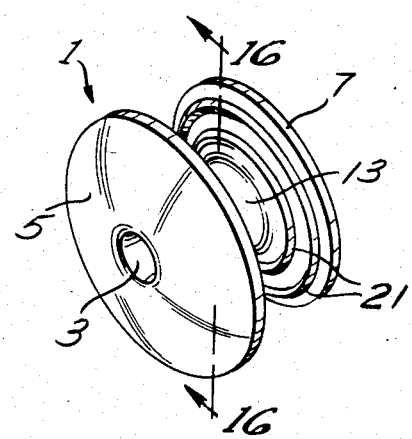
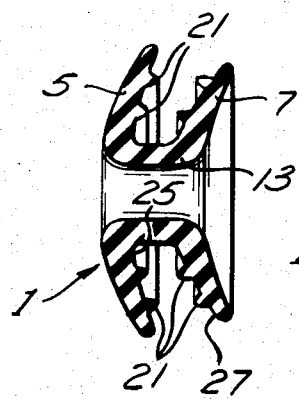
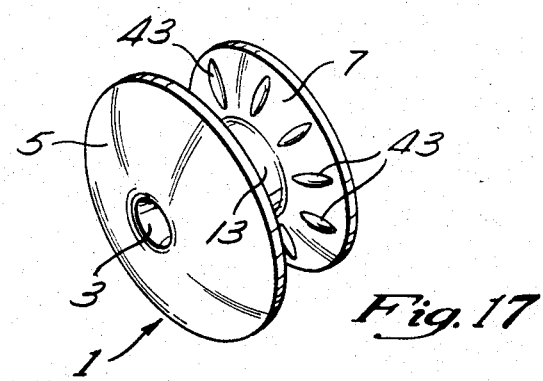
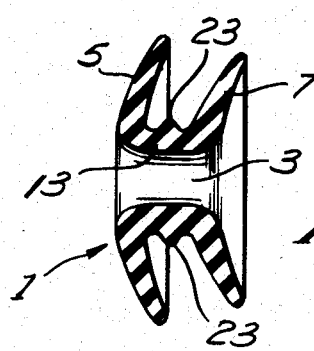
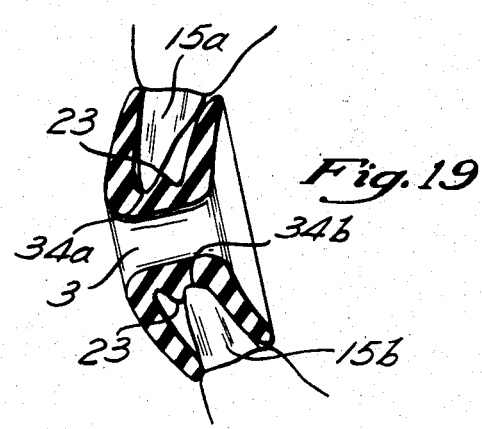

DEVICE FOR CLEANING TEETH AND MASSAGING GUMS

BACKGROUND OF THE INVENTION

The invention relates generally to a device which can be placed between the teeth and manipulated by chewing action to simultaneously clean teeth, cheeks, lips and the tongue and massage the gums.

Although great strides have been made in other areas of health and hygiene, the field of dentistry still relies upon the use of the toothbrush as the principle means for oral hygiene and general tooth care. Although proper use of a toothbrush, combined with the use of dental floss and periodic visits to a dentist, can be an effective means of preventing cavities, pyorrhea and other periodontal disease, it is clear that a large portion of the general population fails to practice satisfactory oral hygiene.

A large part of the failure can be attributed to the fact that a toothbrush is not an effective means of cleaning teeth for a large portion of the population. Certain of the posterior and inside areas of the teeth and gums simply are not readily accessible with a toothbrush. The spreading of dentifrice, unless combined with thorough scrubbing action, does not remove all the plaque from the surfaces of the teeth and from the gums. Studies have shown that the insufficient duration of use and incorrect brushing action with the toothbrush are the reasons that the desired cleaning and gum massaging is not attained for the majority of all people. Thus, there is a need for another device to thoroughly clean the teeth and massage the gums.

Applicants are aware that other devices have been shown which purport to overcome some of the disadvantages of the toothbrush. For example, in U.S. Pat. No. 1,691,785, of Remensnyder, a device is disclosed which massages gums. In U.S. Pat. No. 3,874,084, of Cole, a device is disclosed for cleaning and massaging teeth. Both devices are molded to fit the patient's teeth and gum tissue, and therefore cannot be mass-produced in order to become available to the general public. Furthermore, a striking disadvantage of the disclosed devices is that since they are molded to cover all or a large portion of the chewing surfaces the pressure asserted on them is distributed unevenly on the various surfaces of the teeth and gums. In addition, the design of the devices discourages extended use necessary for effective cleaning and massaging, since the devices are uncomfortable and occupy the entire mouth.

U.S. Pat. No. 2,172,998, of Grout, discloses a device which overcomes some of these disadvantages. Grout provides a resilient spool or reel-shaped device having a solid cylindrical center portion with two essentially identical enlarged end flange portions. Although Grout discloses a device which can be mass-produced and which distributes the chewing pressure over a smaller area of the teeth and gums, it is primarily a gum massaging device. The peripheral edges of the device principally contact the gums and have little contact with the surfaces of the teeth. Any incidental contact with the teeth would be ineffective to provide any significant cleansing action. Furthermore, the device is not shaped to efficiently transmit tooth pressure into side pressure of the cleaning surfaces.

The fact that the prior art devices do not provide effective means for cleaning the teeth and massaging the gums is the most likely factor responsible for the apparent lack of commercial success of any of the devices. Thus, there continues to be a need for a device to provide effective personal oral hygiene.

SUMMARY OF THE INVENTION

The present invention overcomes the limitations of the prior art by providing a device which can be mass produced and which provides effective teeth cleaning and gum massaging while enabling a person using the device to perform other tasks.

Applicants' invention is a spool-shaped device of a resilient, non-toxic material having a generally cylindrical tubular body with an axial bore, and further having first and second enlarged end portions forming flanges on the device. Tooth pressure on the center portion of the generally cylindrical tubular body causes deformation of the axial bore and results in inward deflection of the end flanges. The inner surfaces of the end flanges contact the inside and outside surfaces of the teeth and gums. Repeated chewing action, combined with pressure from a person's tongue and from the inner surfaces of the person's cheeks and lips, causes the inner surfaces of the end flanges to clean the teeth and massage the gums.

In a preferred embodiment of the device, the inner surface of one end flange is concave to generally conform with the outside surfaces of a person's teeth and gums. Similarly, the inner surface of the other end flange is convex to generally conform with the inside surfaces of a person's teeth and gums. The concave and convex surfaces increase the area of surface contact between the flanges and the teeth and gums, and therefore enhance the cleaning and massaging action.

In especially preferred embodiments of the device, the inner surfaces of the end portions are provided with projections and voids which enhance the cleaning action. The projections can be in various forms including thorns, bristles or wipers. The voids are typically indentations on the inner surfaces of the end flanges or holes through the end flanges.

Other preferred embodiments include elevations or projections on the central tubular portion of the device to contact the occlusal surfaces of the teeth and thereby provide additional cleaning action.

BRIEF DESCRIPTION OF THE DRAWINGS

FIG. 1 is a perspective view of an embodiment of the device.

FIG. 2 is a cross-sectional view taken along line 2—2 of FIG. 1.

FIG. 3 is the cross-sectional view of FIG. 2 showing typical dimensions of the portions of the device.

FIG. 4 illustrates the device of FIGS. 1, 2 and 3 in use.

FIG. 5a is a cross-sectional view of the device in use on an incisor or a canine tooth prior to application of tooth pressure.

FIG. 6a is a cross-sectional view of the device in use on a premolar tooth prior to application of tooth pressure.

FIG. 7a is a cross-sectional view of the device in use on a molar tooth prior to application of tooth pressure.

FIG. 5b is a cross-sectional view of the device in use on an incisor or a canine tooth during application of tooth pressure.

FIG. 6b is a cross-sectional view of the device in use on a premolar tooth during application of tooth pressure.

FIG. 7b is a cross-sectional view of the device in use on a molar tooth during application of tooth pressure.

FIG. 8 is a perspective view of an especially preferred embodiment of the device.

FIG. 9 is a cross-sectional view taken along line 9—9 of FIG. 8.

FIG. 10 is an enlarged view of the area 10 of FIG. 8.

FIG. 11 is a cross-sectional view of the device taken along line 11—11 of FIG. 10 showing the thorn-like projection in greater detail.

FIG. 12a is a perspective view of the device in use, showing the action of the thorn-like projection in the area between teeth.

FIG. 12b is a cross-sectional view of the device taken along line 11—11 of FIG. 10, further showing the thorn-like projection in use.

FIGS. 13 and 14 are cross-sectional views of alternative preferred embodiments of the device.

FIG. 15 is a perspective view of an alternate preferred embodiment of the device.

FIG. 16 is a cross-sectional view taken along line 16—16 of FIG. 15.

FIG. 17 is a perspective view of another alternative embodiment of the device.

FIGS. 18 and 19 are a cross-sectional views of the device illustrating an optional feature of the device.

DETAILED DESCRIPTION OF THE PREFERRED EMBODIMENT

FIG. 1 illustrates a preferred embodiment of applicant's device 1. The device 1 comprises a generally cylindrical tubular body with an axial bore 3 therethrough.

As further shown in FIG. 1, the device 1 has two enlarged end portions 5, 7, forming flanges, which result in a spool-shaped structure for the device 1. The device 1 is manufactured from a resilient, non-toxic material which allows the device to flex when pressure is applied to the center portion of the body. Furthermore, the material must have sufficient durability to withstand the repeated chewing action without deteriorating. Typically, the device can be manufactured from an elastomer such as Dow-Corning MDX-4-4210, or the like, having a hardness of approximately 10 to 80 as measured with a Shore schleroscope durometer. Other materials, having hardness ratings higher or lower than the range disclosed, can be substituted so long as the device is comfortable to use, has sufficient resiliency to transmit chewing pressure to the surfaces of the teeth and is durable. The material is preferably a medical grade, non-toxic silicone rubber material such as that used to manufacture heart valves or other implants, or a latex rubber material such as is commonly used in the manufacture of nipples for infant feeding bottles, and the like.

The overall structure of one embodiment of the device 1 is illustrated in the cross-sectional view of FIG. 2. The device 1 has a generally cylindrical tubular body portion 13 which separates the flange portions 5, 7 to enable the device 1 to be placed between the upper and lower teeth.

Typical dimensions of the device are shown in FIG. 3. The dimensions shown are exemplary for a typical adult mouth, and can vary according to the sizes of the teeth and the thicknesses of the gums. As shown, the second flange portion 7 has a smaller diameter $D_2$ than the first flange portion 5, $D_1$, in order to conform with the smaller inside dimensions of the teeth and the roof of the user's mouth. The lingual (inner) gum tissues tend to cover more of the tooth surface. Furthermore, the labial (outer) surfaces of the teeth are larger because of the curvature of the teeth. The smaller diameter $D_2$ of the second flange portion also reduces the interference with the teethridge which forms the lingual portion of the upper arch.

The device 1 is used by placing it between the upper and lower teeth as illustrated in FIG. 4. Cross-sectional views of the device 1 in place are illustrated in FIGS. 5a, 6a and 7a in its unactivated (no pressure applied) state and in FIG. 5b, 6b and 7b in its activated (pressure applied) state. FIGS. 5a and 5b illustrate the device's use with incisor or canine teeth; FIGS. 6a and 6b illustrate its use with premolars; and FIGS. 7a and 7b illustrate its use with molars. Although the device has a varying amount of surface contact with the three types of teeth shown, the device can thoroughly clean each type, as a result of the interaction of the tooth pressure and pressure from the tongue, lips and cheeks. A description of that interaction will be set forth below.

As illustrated in FIG. 5a, the occlusal surfaces 34a, 34b of the teeth 15a, 15b contact the generally cylindrical tubular portion 13 of the device 1. The teeth 15a, 15b and gums 16a, 16b contact the inside surfaces of the flange portions 5, 7 in the free gingiva area 33 of the gums, (i.e., the area where the teeth enter the gum tissue). An important feature of the device 1 is the axial bore 3 which enhances the amount of pressure exerted on the teeth and gums by the flange portions 5, 7. When pressure is exerted by the teeth 15a, 15b, the axial bore 3 collapses at the center of the device 1, causing the flange portions 5, 7 to deflect inwardly as illustrated in FIG. 5b.

Although deflection would occur if the cylindrical body portion 13 was solid, the axial bore 3 causes the deflection from the tooth pressure to be accentuated. This occurs because the pressure does not have to be exerted against solid material between the side walls of the cylinder. Thus, less tooth pressure is required to transfer pressure to the flange portions of the device and user fatigue is therefore reduced while the pressure on the cleaning surfaces is increased.

The inward deflection causes the flange portions to contact the surfaces of the teeth 15a, 15b, creating a scrubbing action as the teeth move. In addition, the inside surface of each flange portion 5, 7 contacts and massages the inside and outside surfaces of the gum tissue 16a, 16b in the free gingiva area 33. Additional pressure is provided by the force of the lips or cheeks (not shown) on the outside surface 29 of the flange portion 5 and the tongue on the outside surface 31 of the end portion 7. The additional pressures from the lips, cheeks and tongue cause the flexible material to conform to the irregular surfaces of the teeth and gums to increase the surface contact.

Thus, referring again to FIGS. 5a, 5b, 6a, 6b, 7a, and 7b, since one device cannot provide a snug fit to each of the three types of teeth illustrated, the additional pressure from the tongue, cheeks and lips on the surfaces of the device contribute to the cleaning action. The material used is specifically chosen for its flexibility, which flexibility allows the additional pressure to increase the amount of surface contact. In particular, when used on the incisor and canine teeth, where the surface contact resulting from the tooth pressure is the least amount, the lips and tongue can exert the greatest amount of pressure. Conversely, in the molar area, where the cheeks and tongue have the least effect, the surface contact caused by the snug fit is the greatest, as shown in FIGS. 7a and 7b.

Repeated chewing action removes deposits on the surfaces of the teeth 15a, 15b. In addition, the contact with the lips, cheeks and tongue will clean the surfaces of those tissues. The chewing action itself exercises the facial muscles and muscles of mastication.

In a preferred embodiment, illustrated in cross-section in FIGS. 2 and 3, the first and second flange portions are dish-shaped. The inside surface 25 of the first flange portion 5 is concave. Similarly, the inside surface 27 of the second flange portion 7 is convex. This is an important feature, since it has been found that the concave and convex slanting inner surfaces of the flange portions 5, 7 provide better surface contact with the teeth and gums when the device 1 is in use. Thus, minimal additional pressure from the lips, cheeks and gums is necessary to provide sufficient surface contact for thorough teeth cleaning and gum massaging.

As illustrated in FIG. 2, the outer surface 29 of the first flange portion 5 and the outer surface 31 of the second flange portion 7, in an especially preferred embodiment, are also convex and concave, respectively, to provide additional comfort to the user, by allowing the lips and tongue to move more freely on the device. Furthermore, the thicknesses of the flange portions 5, 7 are radially tapered from the root to the tip to increase the flexibility of the device.

The device 1 can be rolled to any position in the mouth of the user without requiring any external manipulation of the device. Typically, the user's tongue is used to reposition the device 1 within the mouth. Thus, once placed in the mouth, the device provides hands-free dental and periodontal prophylactic care. The rolling action of the device provides side-to-side cleaning action in addition to the up-and-down cleaning action of the device during chewing.

The device described herein can have textured contact surfaces in order to provide additional cleaning and massaging action.

In an especially preferred embodiment, illustrated in FIGS. 8 and 9, the flange portions include voids 9 and projections 11, both arranged radially around the inside surfaces of the flange portions 5, 7. The voids 9 can be holes through the end portion as shown in FIG. 8 or can be indentations 35 as shown in another embodiment in FIG. 13. The edges of the holes 9 or indentations 35 provide additional surfaces to assist in scraping material from the surfaces of the teeth. Typically, the voids are 3/16" diameter holes with ten holes in the larger flange portion 5 and eight holes in the smaller flange portion 7.

The projections 11 can be of many forms. In one especially preferred embodiment of the device 1, the projections 11 are thorn-shaped and are angled toward the center of the device 1. Typically, the projections 11 are located on the perimeter of the inside surfaces of the end portions 5, 7, with ten projections 11 on the first flange portion 5 and eight projections 11 on the second flange portion 7. The thorn-shaped projections are shown in more detail in the views of FIGS. 10 and 11. As illustrated in FIG. 12a, the projections 11 will project into the areas between the teeth to dislodge material which collects in those areas. As the device 1 is alternately clamped and released by tooth pressure, the projections 11 will dislodge surface material and pull it away from the gum area. The thorns are also useful for efficiently cleaning the relatively inaccessible areas below the free gingiva 33 as illustrated in FIG. 12b.

The voids 9 and projections 11 can be used separately or in conjunction.

FIG. 14 shows an alternative preferred embodiment which includes bristles 19 on the inside surfaces 25, 27 of the flange portions 5, 7. Typically, the bristles would be distributed evenly over the inner surfaces 25, 27 of the flange portions 5, 7. Thus, the device can be used to more closely simulate the brushing action of a tooth brush. However, as explained above, the device can reach the more inaccessible areas of the teeth and gums since it does not have to be manipulated by a brush handle.

FIGS. 15 and 16 are perspective and cross-sectional views which illustrate an alternative preferred embodiment which includes wipers 21 which provide additional scraping edges. Typically, the wipers 21 are continuous projections running circumferentially around the periphery of the inside surfaces 25, 27 of each flange portion 5, 7 as illustrated in FIG. 15. Alternatively, the wipers 21 can be non-continuous (not shown).

FIG. 17 illustrates an alternative embodiment having ridges 43 radially disposed on the inside surfaces 25, 27 of the flange portions 5, 7. The ridges 43 are particularly advantageous to provide additional cleaning action when the device 1 is rolled from tooth to tooth.

FIG. 18 illustrates a raised portion 23 in the center portion of the device. Typically, the raised portion 23 will be a wedge-shaped projection which contacts the occlusal surfaces 34a, 34b of the teeth, as illustrated in FIG. 19, to provide an additional cleaning action to those surfaces. The raised portion 23 is particularly useful for cleaning the occlusal surfaces of the molars and premolars. The raised portion 23 can be a continuous ridge or a series of projections around the circumference of the cylindrical tubular body portion 13.

Although not required for effective use of the device, a dentifrice can be used in combination therewith.

Applicants have disclosed a novel device to assist in effective dental and periodontal care. As described above, the device can be used to provide cleaning of teeth, cheeks, lips and the tongue and massaging of the gums over an extended period of time while freeing the hands for other uses, such as driving, reading, working or showering. In most circumstances the device can be used as a replacement for chewing gum while providing cleaning and massaging action not provided by chewing gum. Since the device reaches areas inaccessible to a normal toothbrush, the quality of the dental and periodontal care provided greatly exceeds that provided by a toothbrush.

Although the preferred embodiments of the present invention have been described and illustrated, it will be obvious to those skilled in the art that various changes and modifications can be made to the present invention without departing from the spirit thereof. Accordingly, the scope of the present invention is deemed to be limited only by the following appended claims.

What is claimed is:

1. A device for simultaneously cleaning teeth and massaging gums, comprising:
   a spool-shaped member formed as a single piece of resilient, non-toxic material, said member comprising:

a central body portion including a central void, said central body portion having a substantially circular outer circumference to facilitate rolling said central body portion between the teeth from tooth to tooth; and first and second substantially circular dish-shaped flange portions extending radially outward from opposite ends of said central body portion, said first flange portion having a concave surface facing said central body portion to generally conform to the labial surfaces of a user's teeth, said second flange portion having a convex surface facing said central body portion to generally conform to the lingual surfaces of a user's teeth;

said central void of said body portion facilitating collapse of said central body portion which induces a closure of said flanges against the teeth and gums of a user so that said inner surfaces of said flanges contact the surfaces of the teeth and gums to thereby clean the surfaces of the teeth and gums by rubbing on said surfaces.

2. The device as defined in claim 1, wherein at least one of the surfaces of the first and second flange portions facing the central body portion has a plurality of circumferentially spaced projections, said projections positioned to contact the surfaces of the teeth and the areas between the teeth.

3. The device as defined in claim 2, wherein the projections are thorn-shaped, said thorn-shaped projections shaped and positioned to dislodge food material from the areas between the teeth and pull the material away from the gum line.

4. The device as defined in claim 2, wherein the projections are bristles.

5. The device as defined in claim 2, wherein the projections are wipers.

6. The device as defined in claim 1, wherein at least one of the inner surfaces of the first and second flange portions has a plurality of circumferentially spaced cavities, the edges of said cavities contacting the surfaces of the teeth upon closure of the flanges to thereby provide a scraping action on the teeth.

7. The device as defined in claim 6, wherein the cavities penetrate through at least one of the first and second flange portions.

8. The device as defined in claim 6, wherein the cavities are indentations in at least one of the surfaces of the first and second flange portions facing the central body portion.

9. The device as defined in claim 1, wherein the outer surface of the central body portion has a plurality of raised portions positioned to contact the occlusal surfaces of teeth.

10. The device as defined in claim 1, wherein the inner surfaces of the first and second flange portions are textured.

11. The device as defined in claim 1, wherein the resilient, non-toxic material is a medical grade silicone rubber.

12. The device as defined in claim 1, wherein the resilient, non-toxic material is latex rubber.

13. The device as defined in claim 1, wherein the surface of said first flange portion facing away from said central body portion is convex and wherein the surface of said second flange portion facing away from said central body portion is concave.

14. The device as defined in claim 1, wherein said first flange portion has a larger outside diameter than said second flange portion.

15. The device as defined in claim 1, wherein the first and second dish-shaped flange portions are radially tapered from the root to the tip to increase the flexibility of the flanges.

16. A method of cleaning teeth and massaging gums, comprising the steps of:

placing a resilient spool-shaped member at a location between the upper and lower teeth of a user, said spool-shaped member having a central body portion having a substantially circular outer circumference surrounding a central void and having attached substantially circular dish-shaped first and second flange portions said first and second substantially circular dish-shaped flange portions extending radially outward from opposite ends of said central body portion, said first flange portion having a concave surface facing said central body portion to generally conform to the labial surfaces of a user's teeth, said second flange portion having a convex surface facing said central body portion to generally conform to the lingual surfaces of a user's teeth;

positioning the teeth on opposite sides of said central body portion between said first and second flange portions;

chewing on said central body portion to intermittently collapse said central body portion, thereby moving said concave inner surface of said first flange portion and said convex inner surface of said second flange portion to engage the labial and lingual surfaces, respectively, of said teeth and gums, to thereby clean said labial and lingual surfaces by rubbing said surfaces of said flange portions on said teeth and gums;

moving said central body portion to a new location in the user's mouth by rolling said central body portion between the user's teeth without manual intervention; and repeating said chewing and moving steps at each of the locations in the user's mouth to be cleaned.

* * * * *